United States Patent [19]

Näf et al.

[11] 4,304,793

[45] Dec. 8, 1981

[54] POLYUNSATURATED ALIPHATIC ESTERS AS FLAVORING INGREDIENTS

[75] Inventors: Ferdinand Näf, Geneva; Wolfgang K. Giersch; Günther Ohloff, both of Bernex, all of Switzerland

[73] Assignee: Firmenich SA, Geneva, Switzerland

[21] Appl. No.: 70,040

[22] Filed: Aug. 27, 1979

[30] Foreign Application Priority Data

Aug. 31, 1978 [CH] Switzerland .......................... 9194/78

[51] Int. Cl.[3] ................................................ A23L 2/26
[52] U.S. Cl. ................................ 426/534; 260/410.9 R
[58] Field of Search ................. 260/410.9 M; 426/534

[56] References Cited

U.S. PATENT DOCUMENTS 4,025,539  5/1977  Fujita et al. .......................... 260/410

OTHER PUBLICATIONS

Winter et al., *Helv. Chim. Acta.* 62, 135–139 (1979).

*Primary Examiner*—John F. Niebling
*Attorney, Agent, or Firm*—Pennie & Edmonds

[57] ABSTRACT

Polyunsaturated aliphatic esters of new chemical structure find utility as flavor modifying agents. Flavoring compositions containing same and process for their preparation.

5 Claims, No Drawings

POLYUNSATURATED ALIPHATIC ESTERS AS FLAVORING INGREDIENTS

SUMMARY OF THE INVENTION

The invention relates to a method for improving, enhancing or modifying the flavouring properties of foodstuffs and beverages which method comprises adding thereto an effective amount of a polyunsaturated aliphatic ester of formula

wherein symbol R represents a lower linear or branched alkyl radical having 1 to 3 carbon atoms and wherein the double bond at position 4 possesses a cis configuration.

The invention relates also to the compounds of formula (I), more particularly it relates to ethyl octa-cis4,7-dien-1-oate.

The invention provides further a foodstuff or a beverage containing as flavouring active ingredient a compound of formula (I).

The invention finally relates to a process for the preparation of the compounds of formula (I) which comprises the following subsequent steps:

a. selectively epoxydizing cycloocta-1,5-diene to give 1,2-epoxy-cyclooct-5-ene,
b. oxidizing the thus obtained compound to give 1-oxo-2-hydroxy-cyclooct-5-ene,
c. treating said keto-alcohol with lead tetracetate in an ethanolic medium to give ethyl 7-formyl-hept-4-en-1-oate,
d. reducing this latter by means of sodium borohydride,
e. esterifying resulting ethyl 8-hydroxy-oct-cis4-en-1-oate to give ethyl 8-acetoxy-oct-cis4-en-1-oate and
f. subjecting said ester to pyrolysis to yield ethyl octa-cis4,7-dien-1-oate and, if desired, transesterifying the said ethyl ester to give the compounds of formula (I) wherein R represents an alkyl radical as defined above other than ethyl.

THE INVENTION

It has now been discovered that the compounds of formula (I) possess useful organoleptic properties and consequently they can be advantageously used in the flavour industry. Compounds (I) develop gustative notes of various nature, namely fruity, and they improve the natural character of exotic fruits, especially of pineapple, passion fruit or even orange. Owing to their specific properties, it is now possible to reconstitute more faithfully the natural taste and aroma of those fruits, namely the typical character of their juices. Compounds (I) can be used advantageously for the aromatization of foodstuffs and beverages of various nature, mainly, however, for the aromatization of dairy products, yogourths for instance, fruit juices and syrups. They can be used moreover as flavouring additives in bakery products, cakes or pastries, in jams, toffees or even chewing-gums wherein the fruity note is desired.

Depending on the nature of the material it is desired to aromatize or on the effect desired, the proportions used may vary within a certain range. Typically, concentrations of from about 0.5 to 50 ppm (parts by weight per million) based on the weight of the flavoured material are satisfactorily used. It has to be understood however that said concentrations are not deemed to represent absolute values and proportions higher or lower than those given above may also be used. The compounds of the invention can be used on their own or, more frequently, in admixture with common edible solvents such as ethanol, dipropylene-glycol or triacetine, or on solid carriers such as gum arabic or dextrine.

Among the compounds of formula (I), ethyl octa-cis4,7-dien-1-oate is preferred when used in accordance with the invention.

Compounds (I) possess also perfuming properties and develop green, fresh, flowery and fruity odour notes.

In accordance with the invention the compounds of formula (I) are prepared by the original process defined above, starting from cycloocta-1,5-diene a commercially available product. The process of the invention is illustrated by the following reaction pathway:

Scheme:

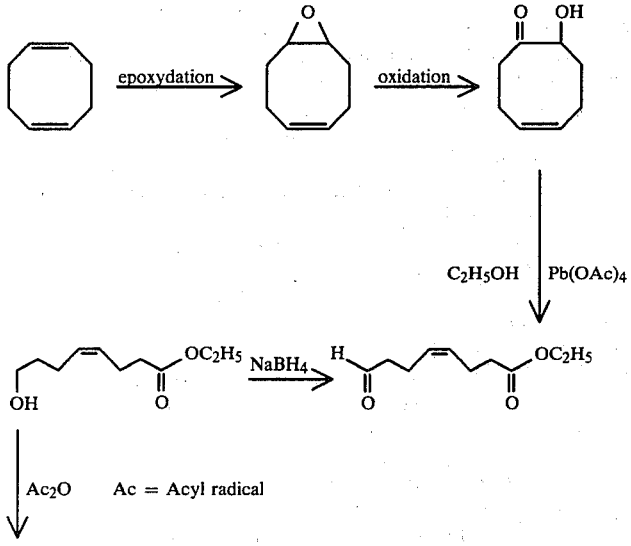

Scheme:

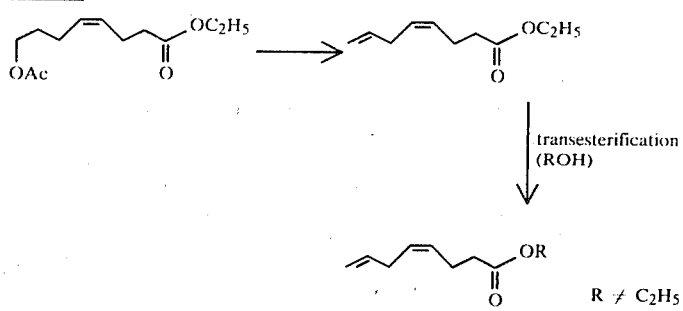

The invention is better illustrated by but not limited to the following examples wherein the temperatures are indicated in degrees centigrade.

EXAMPLE 1

Ethyl octa-cis4,7-dien-1-oate 1. 20 g of m-chloroperbenzoic acid (about 85%) in 1 lt of dichloromethane were added dropwise at about 5° to a solution of 45 g of cycloocta-1,5-diene in 500 ml of dichloromethane. The reaction mixture was then kept 18 h at room temperature, then after filtration, washed with an aqueous solution of sodium sulphite, sodium carbonate and finally with water until neutrality.

By evaporation of the volatiles followed by distillation there were obtained 32 g of a fraction having b.p. 41°/0.01 Torr.

2. The thus obtained substance was dissolved in 150 ml of dimethylsulfoxide and a flow of air was bubbled during 27 h through the solution heated at 110°. The course of the reaction was followed by vapour phase chromatographic analysis. After cooling the reaction mixture was poured onto a mixture of ice-water and extracted with ether. The combined organic extracts were treated as usual by washing, drying, evaporating and distilling them.

21 g of 1-oxo-2-hydroxy-cyclooct-5-ene having b.p. 63°–70°/0.05 Torr were thus obtained.

IR: 3400, 1700 and 835 cm$^{-1}$.

NMR: 1.2–2.9 (8H, m); 3.4 (1H); 4.33 (1H, m); 5.65 (1H, m) δ ppm.

MS: M$^+$ = 140 (3); m/e: 122 (16), 111 (18), 96 (60), 84 (56), 68 (95), 67 (100), 54 (85), 39 (68), 27 (46).

3. 80 g of lead tetracetate were added portion-wise under stirring at room temperature to a solution of 21 g of the hydroxy-ketone, obtained sub. 2, in 500 ml of a 3:7 mixture of ethanol and toluene.

The addition lasted 15 minutes and the temperature of the mixture have increased up to about 35°, then the whole was left to rest for 1½ h. The mixture was filtered and the clear filtrate was washed with an aqueous solution of sodium bisulphite, sodium bicarbonate and a saturated aqueous solution of NaCl. On evaporation and distillation there were obtained 12.2 g of ethyl 7-formyl-hept-cis4-en-1-oate having b.p. 120°/0.1 Torr. The purity of the product was of about 85%.

IR: 2740, 1730 and 855 cm$^{-1}$.

NMR: 1.27 (3H, t, J=7 Hz); 1.5–2.7 (8H, m); 4.17 (2H, q, J=7 Hz); 5.4 (1H, m); 9.77 (1H, m) δ ppm.

MS: M$^+$ = 184 (0); m/e: 141 (40), 110 (15), 95 (22), 81 (33), 67 (100), 55 (49), 41 (69), 29 (67).

4. A mixture of 7 g of the oxo-ester obtained as described above and 2 g of sodium borohydride in 50 ml of ethanol was kept under stirring at room temperature during 2 h. The reaction mixture was then poured onto ice, acidified and extracted with ether, then subjected to the usual treatments of washing, drying and evaporating. A bulb distillation of the residue gave 5.2 g of ethyl 8-hydroxy-oct-cis4-ene-1-oate having b.p. 140° (bath temperature)/0.01 Torr.

IR: 3450, 1740 and 855 cm$^{-1}$.

NMR: 1.23 (3H, t, J=7 Hz); 1.65 (2H, m); 2.02 (1H); 1.9–2.5 (6H, m); 3.67 (2H, J=6 Hz, t); 4.13 (2H, q, J=7 Hz); 5.4 (2H, m) δ ppm.

MS: M$^+$ = 186 (0); m/e: 156 (59), 140 (31), 123 (26), 110 (47), 97 (54), 81 (92), 67 (100), 55 (58), 41 (76), 29 (83).

5. A mixture of 4 g of the above obtained hydroxy-ester, 10 ml of acetic anhydride and 10 ml of pyridine was kept under stirring at room temperature during 2 h. The mixture was then directly subjected to pyrolysis at 450° in a flow of nitrogen. The pyrolysate was dissolved in petrol ether and the solution thus obtained was washed with diluted aqueous HCl, sodium bicarbonate and water. The desired ester was purified by column chromatography on silica gel and bulb distillation and 480 mg were thus obtained b.p. 72°–78°/0.05 Torr.

IR: 3080, 1735, 1640, 920 and 750 cm$^{-1}$.

NMR: 1.25 (3H, t, J=7 Hz); 2.38 (4H, m); 2.82 (2H, t, J=5 Hz); 4.14 (2H, q, J=7 Hz); 4.85–6.15 (5H, m) δ ppm.

MS: M$^+$ = 168 (5); m/e: 122 (14), 94 (51), 80 (100), 79 (76), 67 (30), 55 (19), 41 (41), 29 (38).

EXAMPLE 2

A base flavour composition of fruity type was prepared by mixing the following ingredients (parts by weight):

| | |
|---|---|
| Vanilline | 20 |
| Sweet orange oil | 40 |
| Lemon oil | 10 |
| Amyl acetate | 20 |
| Butyl acetate | 30 |
| Ethyl propionate | 30 |
| Ethyl butyrate | 50 |
| Ethyl valerate | 20 |
| Ethyl oenanthate | 40 |
| Benzyl alcohol | 200 |
| Propylene glycol | 540 |
| | 1000 |

By making use of the above base, two novel compositions were prepared as follows:

|  | Composition A (control) | Composition B (test) |
|---|---|---|
| Base composition | 100 | 100 |
| Ethyl octa-cis4,7-dien-1-oate | — | 35 |
| 95% Ethanol | 900 | 865 |
| Total | 1000 | 1000 |

The novel compositions were subjected to an organoleptic evaluation in an acidified sugar syrup (prepared by dissolving 650 g of saccharose in 1000 ml of water containing 10 ml of a 50% citric acid aqueous solution). The concentration was of 100 g of flavour composition per 100 l of acidified syrup.

The test composition possessed a characteristic pineapple note, which note was not present in the control composition.

What we claim is:

1. A substantially pure polyunsaturated aliphatic ester of formula

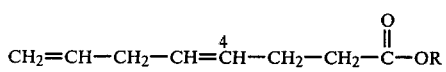

(I)

wherein symbol R represents a lower linear or branched alkyl radical having 1 to 3 carbon atoms and wherein the double bond at position 4 possesses a cis-configuration.

2. Substantially pure Ethyl octa-cis4,7-dien-1-oate.

3. Method for improving, enhancing or modifying the flavouring properties of foodstuffs and beverages which comprises adding thereto an effective amount of a substantially pure polyunsaturated aliphatic ester of formula (I), as set forth in claim 1.

4. A foodstuff or a beverage containing as flavouring active ingredient a substantially pure compound of formula (I), as set forth in claim 1.

5. Process for the preparation of the compounds of formula (I) of claim 1, which comprises the following subsequent steps:
 a. selectively epoxydizing cycloocta-1,5-diene to give 1,2-epoxy-cycloct-5-ene,
 b. oxidizing the thus obtained compound to give 1-oxo-2-hydroxy-cyclooct-5-ene,
 c. treating said keto-alcohol with lead tetracetate in an ethanolic medium to give ethyl 7-formyl-hept-4-en-1-oate,
 d. reducing this latter by means of sodium borohydride,
 e. esterifying resulting ethyl 8-hydroxy-oct-cis4-en-1-oate to give ethyl 8-acetoxy-oct-cis4-en-1-oate and
 f. subjecting said ester to pyrolysis to yield ethyl octa-cis4,7-dien-1-oate and, if desired, transesterifying the said ethyl ester to give the compounds of formula (I) wherein R' represents an alkyl radical as defined above other than ethyl.

* * * * *